(12) United States Patent
Davies et al.

(10) Patent No.: US 11,147,614 B2
(45) Date of Patent: Oct. 19, 2021

(54) ELECTROSURGICAL DEVICE HAVING A DISTAL APERTURE

(71) Applicant: Baylis Medical Company Inc., Montreal (CA)

(72) Inventors: Gareth Davies, Toronto (CA); John Paul Urbanski, Toronto (CA); Mahmood Mirza, Toronto (CA); Ellen Harfield, Mississauga (CA)

(73) Assignee: Baylis Medical Company Inc., Mississauga (CA)

( * ) Notice: Subject to any disclaimer, the term of this patent is extended or adjusted under 35 U.S.C. 154(b) by 0 days.

(21) Appl. No.: 16/929,270

(22) Filed: Jul. 15, 2020

(65) Prior Publication Data

US 2020/0345410 A1 Nov. 5, 2020

Related U.S. Application Data

(63) Continuation of application No. 14/850,545, filed on Sep. 10, 2015, now Pat. No. 10,751,115, which is a
(Continued)

(51) Int. Cl.
*A61B 18/14* (2006.01)
*A61B 90/00* (2016.01)
*A61B 18/00* (2006.01)

(52) U.S. Cl.
CPC ............... *A61B 18/1477* (2013.01); *A61B 2018/00083* (2013.01); *A61B 2018/00297* (2013.01);
(Continued)

(58) Field of Classification Search
CPC ... A61B 2018/1425; A61B 2018/1427; A61M 2205/192; A61M 2205/195; A61M 2205/197
See application file for complete search history.

(56) References Cited

U.S. PATENT DOCUMENTS 8,192,425 B2 * 6/2012 Mirza ............... A61B 18/1482
606/41
2006/0224156 A1 10/2006 Arts et al.
(Continued)

FOREIGN PATENT DOCUMENTS

| EP | 0651974 A2 | 5/1995 |
| EP | 0651974 A3 | 5/1995 |
| JP | H07504594 A | 5/1995 |
| JP | 2009131565 A1 | 6/2009 |
| JP | 2012090999 A1 | 5/2012 |
| WO | 2005046739 A2 | 5/2005 |

(Continued)

OTHER PUBLICATIONS

Patent Cooperation Treaty, International Preliminary Report on Patentability, International Application No. PCT/IB2014/064600, dated Sep. 13, 2016.
(Continued)

*Primary Examiner* — Ronald Hupczey, Jr.
(74) *Attorney, Agent, or Firm* — Glenn Arnold; Samuel Tekie; Vincent Man (57) ABSTRACT

A method and apparatus are disclosed for providing forward fluid delivery through an energy delivery device that avoids coring when it delivers energy to a tissue. The device has a distal face defining an opening, with the distal face including at least one electrically exposed portion and at least one electrically insulated portion. An embodiment of the energy delivery device includes an elongate member defining a lumen structured to receive a fluid, and a distal face defining an aperture in communication with the lumen. The distal face includes an electrically exposed conductive portion and an electrically insulated portion. The electrically exposed conductive portion is configured such that the energy it delivers while the energy delivery device is advanced into a tissue punctures the tissue without the tissue substantially occluding the lumen and without creating embolic particles.

20 Claims, 9 Drawing Sheets

Related U.S. Application Data continuation-in-part of application No. PCT/IB2014/059641, filed on Mar. 11, 2014.

(60) Provisional application No. 61/787,617, filed on Mar. 15, 2013.

(52) U.S. Cl.
CPC ............ *A61B 2018/00351* (2013.01); *A61B 2018/1427* (2013.01); *A61B 2018/1497* (2013.01); *A61B 2090/392* (2016.02); *A61B 2090/3966* (2016.02); *A61B 2218/002* (2013.01)

(56) References Cited

U.S. PATENT DOCUMENTS

| | | | | |
|---|---|---|---|---|
| 2008/0086120 | A1* | 4/2008 | Mirza | A61B 18/1482 606/41 |
| 2008/0086121 | A1* | 4/2008 | Sensenbrenner | A61B 18/1482 606/50 |
| 2012/0172857 | A1 | 7/2012 | Harrison et al. | |

FOREIGN PATENT DOCUMENTS

| | | | | |
|---|---|---|---|---|
| WO | 2005046739 | A3 | 5/2005 | |
| WO | 2010135793 | A1 | 12/2010 | |
| WO | WO-2010135793 | A1 * | 12/2010 | ......... A61B 18/1477 |
| WO | 2011146243 | A1 | 11/2011 | |

OTHER PUBLICATIONS

Patent Cooperation Treaty, International Preliminary Report on Patentability, International Application No. PCT/IB2014/059641, dated Sep. 15, 2015.

Japanese Office Action for counterpart to parent Japanese Application No. 2015-562485, dated Jan. 23, 2018.

European Patent Office, Communication pursuant to Rules 161(2) and 162 EPC, for counterpart to parent European Application No. 147885380.7, dated Oct. 25, 2016.

Applicant's Reply to Communication pursuant to Rules 161 and 162 for counterpart to parent European Application No. 147885380.7, dated Apr. 30, 2017.

European Patent Office, Communication pursuant to Rule 70(2) and 70a(2) EPC for counterpart to parent European Application No. 14763885.2, dated Oct. 27, 2016.

Applicant's Reply to Communication pursuant to Rule 70 EPC for counterpart to parent European Application No. 14763885.2, dated May 8, 2017.

European Patent Office, Communication pursuant to Rules 161(2) and 162 EPC, for counterpart to parent European Application No. 14763885.2, dated Oct. 22, 2015.

Applicant's Reply to Communication pursuant to Rules 161 and 162 for counterpart to parent European Application No. 14763885.2, dated Apr. 21, 2016.

Supplementary European Search Report for European Application No. 14763885.2, dated Sep. 28, 2016.

Supplementary European Search Report for European Application No. 14885380.7, dated Oct. 18, 2017.

European Patent Office, Communication pursuant to Rule 70(2) and 70a(2) EPC for counterpart to parent European Application No. 147885380.7, dated Nov. 7, 2017.

Applicant's Reply to Communication pursuant to Rule 70 EPC for counterpart to parent European Application No. 147885380.7, dated May 17, 2018.

Japanese Search Report for counterpart to parent Japanese Application No. 2015-562485, dated Jan. 26, 2018.

Japanese Search Report Translation for counterpart to parent Japanese Application No. 2015-562485, dated, Jan. 26, 2018.

* cited by examiner

ELECTROSURGICAL DEVICE HAVING A DISTAL APERTURE

CROSS-REFERENCES TO RELATED APPLICATIONS

This application is a continuation of U.S. application Ser. No. 14/850,545, filed Sep. 10, 2015, which is a continuation in part of international application PCT/IB2014/059641, filed Mar. 11, 2014, which claims the benefit of U.S. provisional application No. 61/787,617, filed Mar. 15, 2013. All of the aforementioned applications are hereby incorporated by reference in their entirety.

TECHNICAL FIELD

The disclosure relates to methods and devices usable to deliver energy within the body of a patient. More specifically, the present invention is concerned with an electrosurgical perforation apparatus.

SUMMARY

Disclosed herein are embodiments of an energy delivery device providing forward fluid delivery while avoiding coring, the device comprising a distal face defining an opening, the distal face including at least one electrically exposed portion and at least one electrically insulated portion.

In one broad aspect, embodiments of the present invention include an energy delivery device comprising an elongate member which comprises a non-conductive material and defines a lumen for receiving a fluid, a distal face of the elongate member being beveled and defining an aperture in communication with the lumen, the distal face including at least one electrically exposed conductive portion and at least one electrically insulated portion wherein the electrically exposed conductive portion is lateral to the aperture and the electrically insulated portion extends radially from a wall of the aperture to a periphery of the distal face. This configuration of the distal face avoids creation of emboli upon delivery of energy via the electrically exposed conductive portion.

As a feature of the one broad aspect, the electrically exposed conductive portion comprises a distal surface of an electrode located at a distal portion of the distal face. In some such embodiments, the distal surface of the electrode is generally crescent-shaped. Some embodiments of the first broad aspect further comprise a wire electrically coupled to the electrode, the wire being operable to convey energy to the electrode, with some examples including the wire being embedded in a sidewall of the elongate member. Typical embodiments of the first broad aspect include the electrically insulated portion comprising a polymer located at a proximal portion of the distal face. In some such embodiments, the electrically insulated portion encircles the aperture.

In some embodiments of the first broad aspect, the elongate member has a length of about 30 cm to about 100 cm to facilitate a puncture of a septum of a heart. In some embodiments, the elongate member has an outer diameter of about 0.40 mm to about 1.5 mm to minimize hemodynamic instability upon puncturing tissue.

In some embodiments of the first broad aspect, the elongate member has a flexural rigidity of at least about 0.016 $Nm^2$, with some specific embodiments having an elongate member with a flexural rigidity of about 0.017 $Nm^2$.

Some embodiments of the first broad aspect further comprise a radiopaque marker for marking a location of the electrode, with some examples having the marker embedded in a sidewall of the elongate member.

In some embodiments of the first broad aspect, the elongate member comprises a curved section. In some such embodiments, the curved section has a curve length from about 10 cm to about 25 cm and traverses from about 20° to about 40° of a circle, while in other embodiments, the curved section has a curve length from about 4 cm to about 7 cm and traverses from about 70 degrees to about 110 degrees of a circle.

Some embodiments of the first broad aspect further comprise a handle coupled to a proximal end of the elongate member. In some such embodiments, the handle comprises an electrical connector operable to be coupled to an electrosurgical generator. Some embodiments include the handle comprising a fluid port for allowing for fluid communication between the lumen and a source of fluid. In some examples, the handle comprises at least one orientation indicator for indicating a direction of a curve of a curved section of the elongate member. Some embodiments of the handle comprise a plurality of ridges for transmitting tactile feedback In a further broad aspect, embodiments of the present invention include a method of puncturing tissue comprising the steps of (a) delivering energy through a first portion of a distal face of an energy delivery device to tissue at a target site to create a puncture through the tissue, while preventing delivery of energy from a second portion of the distal face; and (b) advancing the energy delivery device through the tissue by pushing aside a flap of tissue defined by the puncture.

Another broad aspect of the invention is for an energy delivery device comprising an electrically conductive tubular member at least partially covered by electrically insulating material, wherein the tubular member defines a lumen for receiving a fluid, and a distal face of the tubular member defines an aperture in communication with the lumen and includes at least one electrically exposed conductive portion and at least one electrically insulated portion. With this configuration, energy delivered to a tissue via the at least one electrically exposed conductive portion results in a puncture having a shape substantially corresponding to a shape of the electrically conductive portion of the distal face.

In another broad aspect, embodiments of the invention are for an energy delivery device comprising an elongate member defining a lumen for receiving a fluid, a beveled distal face of the elongate member defining an aperture in communication with the lumen, and the beveled distal face including at least one electrically exposed conductive portion and at least one electrically insulated portion.

In yet another broad aspect, embodiments of the invention are for an energy delivery device comprising an elongate member defining a lumen for receiving a fluid, and a distal face defining an aperture in communication with the lumen, wherein the distal face includes at least one electrically insulated portion and at least one electrically exposed conductive portion configured to puncture through a tissue at a target site upon delivery of energy substantially without coring tissue from the target site.

BRIEF DESCRIPTION OF THE DRAWINGS

In order that the invention may be readily understood, embodiments of the invention are illustrated by way of examples in the accompanying drawings, in which.

DETAILED DESCRIPTION

Devices used for puncturing tissue, such as the septal tissue of a patient's heart, are typically either mechanical or electrosurgical in nature. Mechanical force is typically used with a conventional Brockenbrough transseptal needle to create a puncture. The Brockenbrough needle has a sharp beveled tip and a forward-facing aperture that may be used for injecting fluid or monitoring pressure. Under certain circumstances, however, mechanical force is not always effective at puncturing tissue. In such cases, physicians have proposed using an electrocautery generator or the like to electrify the mechanical needle and thereby produce an ad hoc electrosurgical device with a forward facing aperture. One drawback to electrifying a Brockenbrough needle is the risk of tissue coring. A core (or plug) of tissue is typically cut from the tissue inside the ring-shaped distal tip of the needle upon delivery of energy. This tissue core is subsequently captured in the lumen of the electrosurgical device upon advancement of the needle through tissue. The tissue core may be released from the lumen, potentially leading to emboli and increasing the risk of a stroke or other ischemic event. Furthermore, a non-insulated and electrified Brockenbrough needle bears an additional increased risk of burns to the patient and physician.

Some dedicated electrosurgical puncturing devices have solid distal electrodes and incorporate side-ports instead of a forward-facing lumen aperture. While the solid distal electrode avoids the risk of tissue coring, without a forward-facing lumen aperture, such devices lack the ability to effectively inject fluid to stain the target tissue, or monitor fluid pressure when confined inside the lumen of a close-fitting dilator. In addition, while it is possible in some cases for a guide-wire to be passed through or to be received by a side-port, in general, devices lacking a forward facing aperture do not facilitate the cooperative use of a guide-wire. In contrast, devices with a forward facing aperture are typically more effective at injecting fluid, monitoring pressure, and facilitating cooperative use of a guide-wire.

Thus, the present inventors have conceived and reduced to practice an energy delivery device for puncturing tissue, such as an atrial septum of a heart, configured to reduce the risks of tissue coring and embolus formation while still comprising a forward facing lumen aperture to provide for pressure monitoring, forward fluid delivery, and cooperative use with a guide-wire. The device comprises a distal face that defines an opening and includes an electrically exposed portion and an electrically insulated portion extending radially from the opening to the periphery of the distal face. Typical embodiments can be advanced over a guide-wire to a treatment site.

In particular, the described embodiments are configured such that an electrode used for puncturing tissue does not completely encircle or enclose a forward facing lumen aperture, thereby avoiding a ring-shaped electrode configuration that may possibly core tissue. Ring-shaped electrodes are typically circular, but non-circular ringed electrodes (e.g. square-shaped, elliptical-shaped) are also possible. For explanatory purposes, this disclosure generally describes ring-shaped electrodes as being circular. Furthermore, while this disclosure describes electrosurgical devices that are generally circular in cross-section, the concepts and claims of this disclosure also apply to non-circular devices.

Some embodiments of the present invention comprise a device having a metallic tube operable to deliver energy in which a portion of the tube's distal (forward facing) surface is insulated to interrupt the creation of a ring-shaped electrode (i.e. the electrode only partially encircles the forward facing lumen aperture). In some embodiments, the distal surface of the electrode (the cutting surface) is situated substantially lateral to the front opening, such that the electrode does not encircle the front opening. In typical embodiments, the outer perimeter of the electrode defines a portion, but not all, of the outer perimeter of the distal face of the disclosed energy delivery device. As such, the device is configured to create a puncture corresponding with a portion (but not all) of the outer perimeter of the distal face. Typically, the puncture defines a flap of tissue which the beveled distal face pushes aside when the user advances the device. In some embodiments, the distal surface of the electrode defines a generally semicircular or C-shaped configuration.

With specific reference now to the drawings in detail, it is stressed that the particulars shown are by way of example and for purposes of illustrative discussion of certain embodiments of the present invention only. Before explaining embodiments of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1:
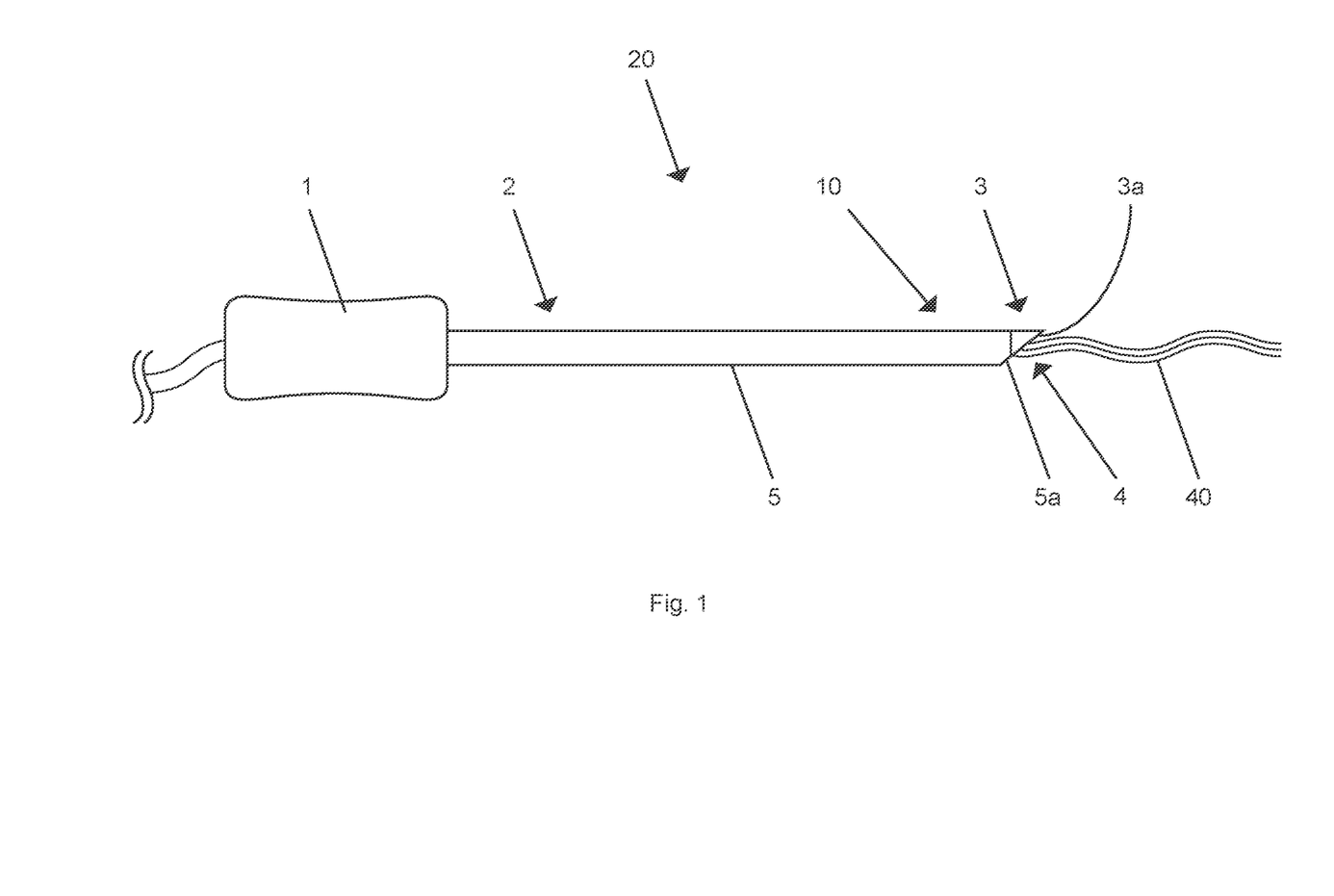
FIG. 1 is an illustration of an embodiment of a device including a handle and shaft.

FIG. 1 is an illustration of an embodiment of a device including a handle and shaft. FIG. 1 includes energy delivery device 20 comprised of elongate member 2, electrically insulating material 5, and distal portion 10. The handle 1 is mechanically coupled to the proximal end of the elongate member 2. Elongate member 2 defines a lumen. Distal portion 10 includes electrode 3 and distal face 4 (further described herein below), which defines an aperture. The embodiment is operable to direct a fluid forward, as represented by fluid flow lines 40, and facilitate cooperative use with a guide-wire.

In some embodiments, elongate member 2 has a length of about 30 cm to about 100 cm to facilitate the puncture of a septum of a heart. In some embodiments, the elongate member has an outer diameter of about 0.40 mm to about 1.5 mm to minimize hemodynamic instability once energy delivery device 20 is removed from the patient. In some embodiments, the energy delivery device 20 is a stiff elongate needle.

Some embodiments of energy delivery device 20 include an elongate member 2 having flexural rigidity of at least about 0.016 Nm², for example a flexural rigidity of about 0.017 Nm², to provide tactile feedback for a user.

Figure 9A:
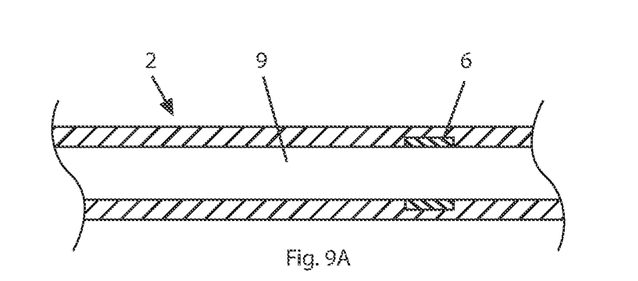
FIGS. 9a and 9b illustrate examples of embedded markers.
Figure 9B:
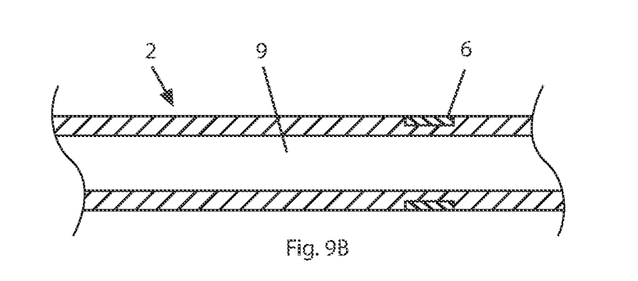

Some embodiments of the energy delivery device have markers for highlighting the location of important landmarks. Such landmarks may include the location where the elongate member 2 begins to curve, the location of the electrode 3, or the location of the proximal edge of a beveled distal face. In some embodiments the marker is radiopaque. FIGS. 9a and 9b illustrate examples of markers 6 embedded in the sidewall of elongate member 2. FIG. 9a is an example of an embodiment in which a marker 6 is embedded in the inside surface of the sidewall of elongate member 2. In this configuration, fluid can flow through lumen 9 without being obstructed and the outer diameter of elongate member 2 is not increased. Marker 6 can be embedded in the inside sidewall using different techniques, such as overmoulding. FIG. 9b is an example of an embodiment in which a marker 6 is embedded in the outside sidewall of elongate member 2, which also allows fluid flow through lumen 9 without being obstructed and does not increase the outer diameter of elongate member 2. Imaging marker 6 can be different shapes including, but not limited to, a ring-shaped hollow band or a coil. Alternative embodiments include imaging markers that are disc-shaped, rectangular, elongate, and that define other geometric shapes or symbols.

For the embodiments of FIGS. 9a and 9b, elongate member 2 can be comprised of one or more layers/components of plastic, other polymers, metal, or other materials. The marker is embedded in a sidewall which may be either all metal or substantially (mostly) metal. For example, the marker receiving sidewall can be covered with a relatively thin layer of polymer, such as a layer of electrical insulation. As all metals are radiopaque to some degree, in order to function properly, a radiopaque marker should be more radiopaque than the sidewall. In general, for any embodiment of the device having a radiopaque marker, the radiopaque marker may be comprised of a material that is more radiopaque than the material of the elongate member 2. In FIGS. 9a and 9b, the distal end of lumen 9 is open. Embodiments of FIGS. 9a and 9b having a metal shaft can optionally have a layer of electrically insulating material 5 (not shown in FIG. 9).

While the embodiment of FIG. 1 has a generally straight elongate member 2, in alternative embodiments, the elongate member comprises a curved section. In some examples, the curved section has a curve length from about 10 cm to about 25 cm and traverses from about 20° to about 40° of a circle. In some other examples, the curved section has a curve length from about 4 cm to about 7 cm and traverses from about 70° to about 110° of a circle.

Figure 8:
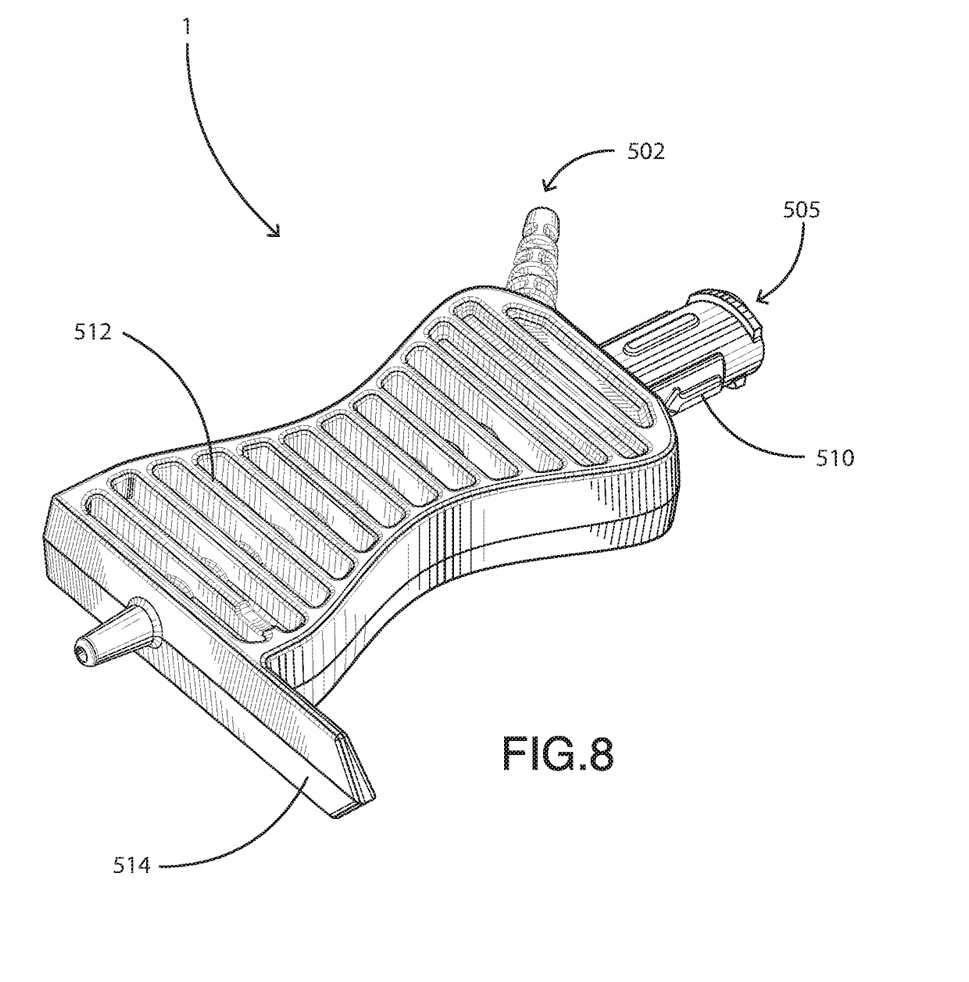
FIG. 8 is an embodiment of a handle.

FIG. 8 illustrates an exemplary handle 1. Handle 1 comprises connector 502 for receiving an electrical plug or other electrical connector, and fluid port 505 for receiving a second connector, for example, a Luer lock. Electrical energy may be delivered from an energy source, through a connector 502 and, typically, a wire (not shown in the drawing) located within handle 1. The electrical energy is then conveyed to the elongate member 2 and electrode 3.

In the embodiment of FIG. 8, the handle 1 includes a relatively large graspable surface having ridges 512 to transmit tactile feedback to the user relatively efficiently, for example, by transmitting vibrations.

The embodiment of FIG. 8 further comprises an orientation indicator 510 located on one side of the handle, in particular, on the part of the handle housing fluid port 505. Orientation indicator 510 indicates the direction of the curve of elongate member 2. The direction of the curve is also indicated by flange 514. In alternative embodiments, orientation indicators comprise inks, etching, or other materials that enhance visualization or tactile sensation.

In some embodiments, tubing is operatively coupled to fluid port 505 of handle 1 at one end, and to a source of fluid such as a syringe, pump, intravenous fluid bag, etc. (not shown in drawing) at the other end. As the fluid port 505 is in fluid communication with lumen 9 of elongate member 2 via a conduit in the handle (not shown), the tubing and lumen 9 are in fluid communication with one another, thus allowing for fluid flow between an external source of fluid and lumen 9.

In some embodiments, aperture 7 and the lumen 9 together provide a pressure transmitting lumen which is coupled via external tubing to a pressure sensing device, for example, a pressure transducer.

Figure 2:
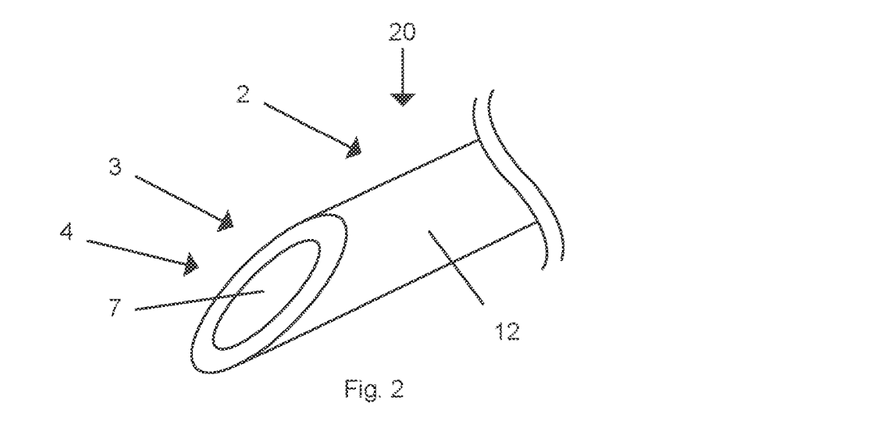
FIG. 2 is an illustration of an electrically conductive tubular member with an angled front face.

Referring now to FIG. 2, the illustration shows an embodiment of an electrosurgical device initially lacking electrical insulation over its distal face. The device includes an electrically conductive tubular member 12 with an angled or beveled front face (distal face 4). As previously described, the distal (or front) surface of a device configured as illustrated in FIG. 2 may function as a ring-shaped electrode when delivering electrical energy to tissue, thereby coring out a plug of tissue having a circumference defined by aperture 7. Configuring a portion of the distal surface to be non-conductive may reduce or eliminate the risk of coring tissue, as described further herein below.

Figure 3A:
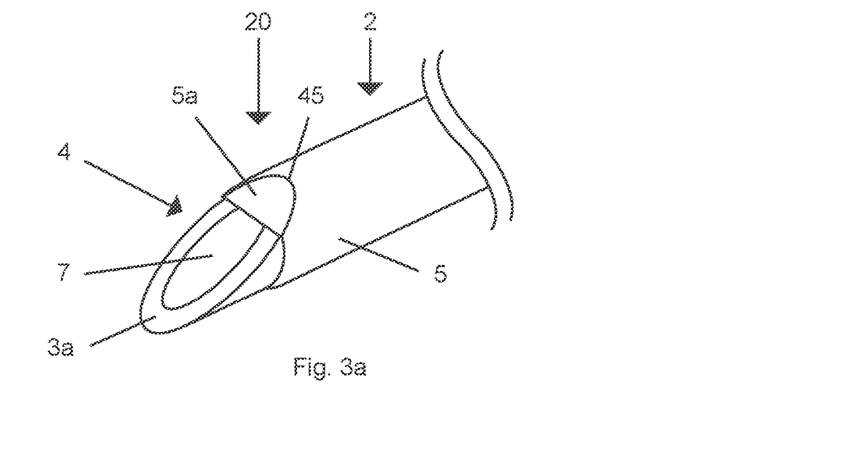
FIGS. 3a to 3c are illustrations of an embodiment of a device with an electrically conductive tubular member and insulation.
Figure 3B:
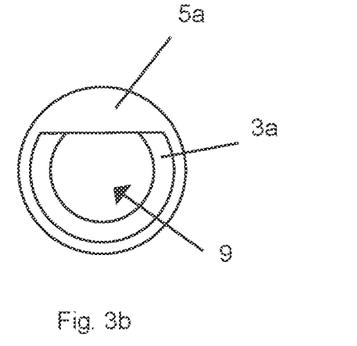
Figure 3C:
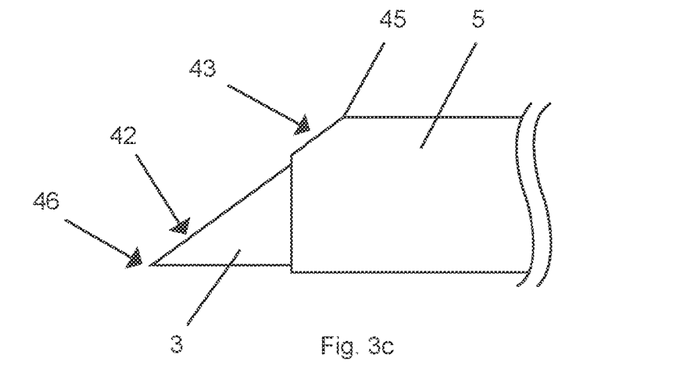

FIGS. 3a to 3c illustrate the distal portion of an embodiment of an energy delivery device 20 having an electrically conductive tubular member. Energy delivery device 20 comprises an elongate member 2 which defines a lumen 9 for receiving a fluid, and a distal face 4 which defines an aperture 7 in communication with the lumen. The fluid within the lumen may be injected, withdrawn, or may remain substantially stationary. The electrically conductive tubular member is at least partially covered by electrically insulating material 5, with a distal portion of the electrically conductive tubular member uncovered (i.e. electrically exposed) to define electrode 3. In some embodiments, the electrically conductive tubular member is comprised of stainless steel.

In the embodiment of FIG. 3, distal face 4 is beveled and is comprised of an electrically exposed conductive portion 3a and an electrically insulated portion 5a. The electrically exposed conductive portion 3a is comprised of the distal surface of electrode 3 which, in this embodiment, is generally C-shaped when viewing the distal face head-on (as shown in FIG. 3b). The electrically exposed conductive portion 3a does not completely encircle, circumscribe, or enclose aperture 7, but rather partially surrounds the aperture. Electrically exposed conductive portion 3a defines the distal portion of distal face 4.

The proximal portion of distal face 4 is comprised of electrically insulated portion 5a. Electrically insulated portion 5a extends radially from a wall of the aperture 7 to a periphery 45 of distal face 4 (i.e. extending from the center outwardly or from the circumference inwardly). In some embodiments, the electrically insulated portion of distal face 4 is comprised of polymer insulation, which may be a heat shrink, a spray coating, or a material selectively coated by vapor deposition. In some alternative embodiments, electrically insulated portion 5a comprises a ceramic. In some embodiments, the distal face of the electrically conductive tubular member has a step recess wherein a layer of insulation is received to provide for a planar distal face 4 (i.e. to avoid having a stepped surface).

The electrically exposed conductive portion 3a is configured such that, when a user advances the energy delivery device into a tissue, energy delivered by the electrically exposed conductive portion 3a punctures the tissue without the tissue substantially occluding lumen 9. In particular, the leading surface of electrode 3 defines the cutting surface (i.e. electrically exposed conductive portion 3a) that cuts into tissue when the user advances the energy delivery device while delivering energy. Electrically exposed conductive portion 3a does not completely encircle the forward facing lumen aperture 7, thereby avoiding a ring-shaped (i.e. closed-loop) electrode that could core tissue. Electrically insulated portion 5a interrupts the distal surface of electrically conductive tubular member 12 to prevent the formation of a ring-shaped electrode such that the cutting surface of the electrode only partially encircles aperture 7. The outer perimeter of the distal surface of electrode 3 defines a portion (but not all) of the perimeter of distal face 4, whereby the device creates a puncture corresponding with a portion (but not all) of the perimeter of the distal face, such that the puncture defines a flap of tissue which the beveled distal face pushes aside as the user advances the device through the puncture.

The present inventors tested embodiments of the invention having the configuration of FIG. 3 and found them to puncture tissue substantially without coring. The testing revealed that FIG. 3 embodiments cut C-shaped punctures that correspond to the shape of the electrode, resulting in a flap of skin that is displaced sideways by the proximal portion of distal face 4 when the user advances the energy delivery device 20 to dilate the C-shaped puncture. The inventors also tested electrified Brockenbrough needles, and found them to core tissue when puncturing.

While the embodiment of energy delivery device 20 of FIG. 3 includes a distal tip 46 which is generally sharp, in alternative embodiments it is substantially rounded or atraumatic, such as in the example of FIG. 5. It is not necessary for energy delivery device 20 to have a sharp tip on the device for puncturing. A rounded tip reduces the risk of accidental tissue puncture and skiving of supporting dilators. In such embodiments, the distal portion of the distal face is substantially rounded and, typically, the planar surface of distal face 4 is substantially atraumatic.

Figure 4:
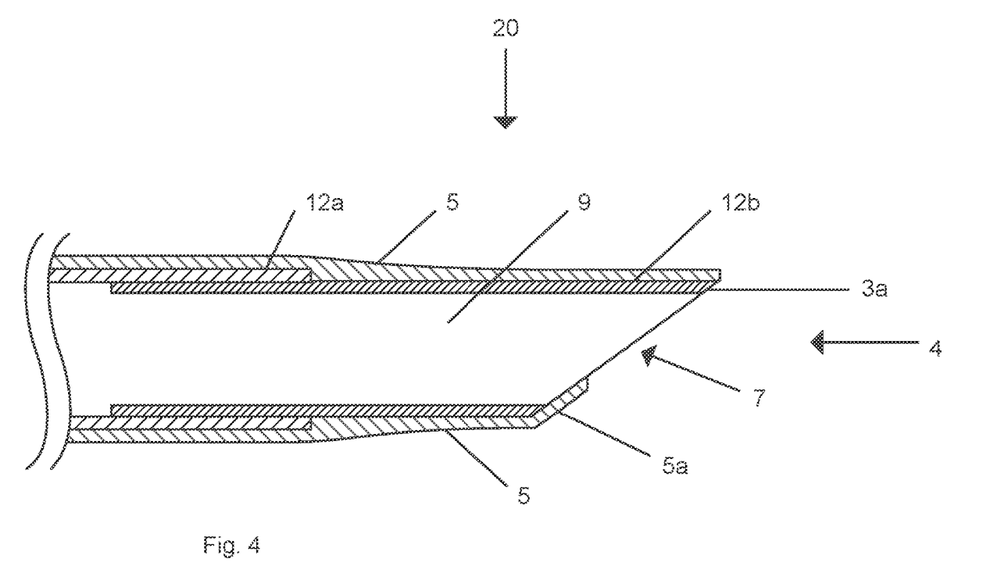
FIG. 4 is an illustration of an alternative embodiment in which an electrically conductive tubular member is comprised of proximal and distal components.

FIG. 4 illustrates another embodiment of an energy delivery device 20 having an electrically conductive tubular member. The embodiment of FIG. 4 includes the electrically conductive tubular member being comprised of two parts, a proximal electrically conductive tubular member 12a, and a distal electrically conductive tubular member 12b which fits into the proximal tubular member. The two tubular members are joined together in any suitable manner, for example, welding, soldering, friction fitting, or with the use of adhesives.

This embodiment also includes electrically insulating material 5 extending to the end of the outer surface of distal electrically conductive tubular member 12b to help minimize electrical leakage. Electrically insulating material 5 extends to cover a portion of the distal end surface of electrically conductive tubular member 12b to define electrically insulated portion 5a of distal face 4. In some alternative embodiments, electrically insulated portion 5a is comprised of a different material than the insulating material 5 that covers the sidewalls of electrically conductive tubular members 12a and 12b.

Similar to the embodiment of FIG. 3, the embodiment of FIG. 4 has an electrically exposed conductive portion 3a which is generally C-shaped. The embodiment of FIG. 4 functions in substantially the same manner as the embodiment of FIG. 3. Details of a similar tube-in-tube configuration are disclosed in co-pending application U.S. application Ser. No. 13/468,939, filed May 10, 2012, and incorporated herein by reference in its entirety.

Figures 5A, 5B:
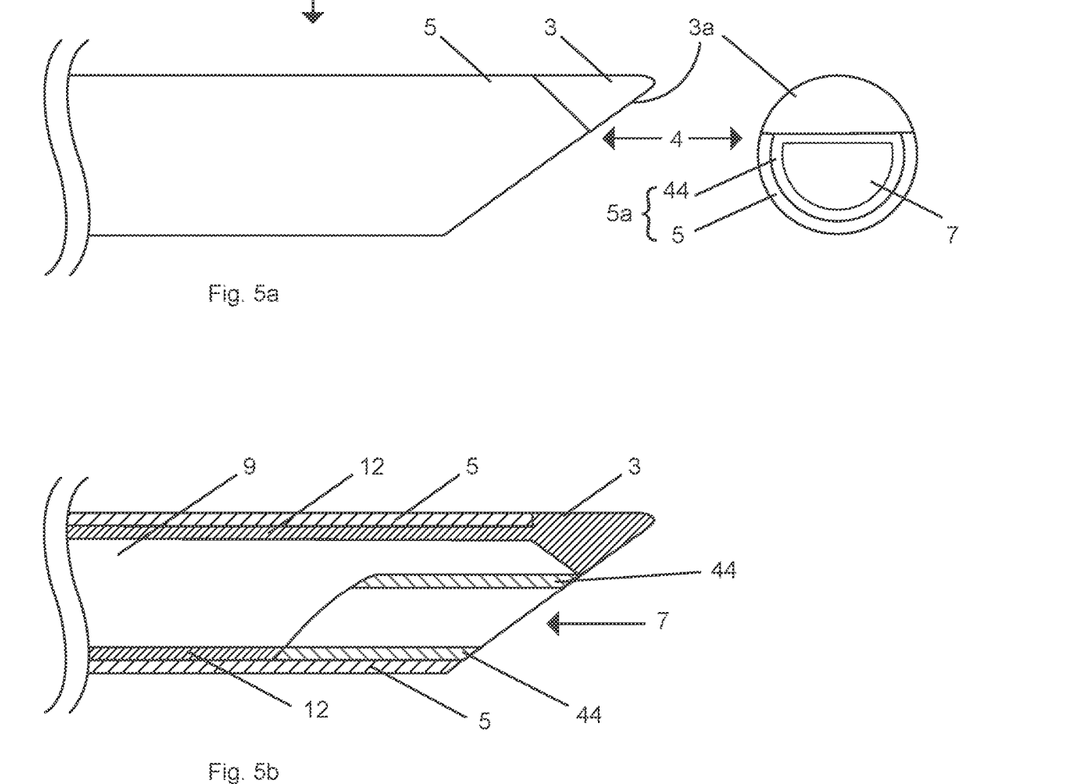
FIGS. 5a to 5c are illustrations of another alternative embodiment in which an electrically conductive tubular member receives a non-conductive insert and insulation.
Figure 5C:
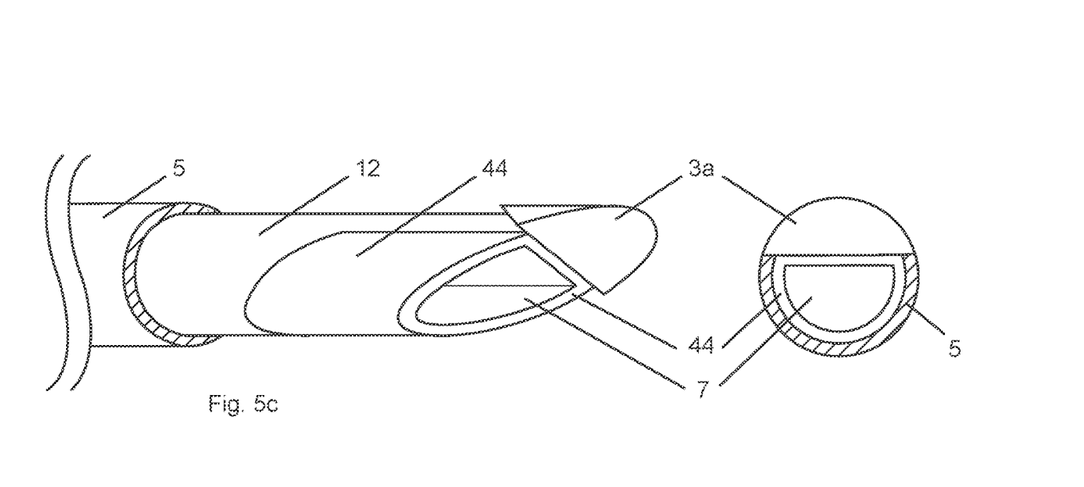

FIGS. 5a to 5c illustrate another embodiment of energy delivery device 20 with an electrically conductive tubular member. The energy delivery device of FIG. 5 includes a recess cut away from a portion of the distal end of electrically conductive tubular member 12, and a non-conductive insert 44 located in the cut-away portion. Typically, non-conductive insert 44 is a polymer. In some embodiments, non-conductive insert 44 is a stiff plastic, and in some particular embodiments, is re-flowed PEP (Fluorinated ethylene propylene). The rotated side-view of FIG. 5c illustrates the device with electrically insulating material 5 partially cut away to show how electrically conductive tubular member 12 receives non-conductive insert 44.

The end view of FIG. 5a shows the non-conductive insert 44 located between a layer of electrically insulating material 5 and electrode 3. The electrically insulated portion 5a of distal face 4 is comprised of the end surfaces of both electrically insulating material 5 and non-conductive insert 44. Non-conductive insert 44 fits into the recess in electrically conductive tubular member 12, and insulating material 5 encloses both conductive insert 44 and electrically conductive tubular member 12, as shown in FIGS. 5b and 5c.

In the embodiment of FIG. 5, electrode 3 is an electrically exposed portion of electrically conductive tubular member 12. In other words, the electrode is continuous with conductive tubular member 12 and is not covered by electrically insulating material 5, as shown in the cross-sectional side-view of FIG. 5b.

Electrically exposed conductive portion 3a is comprised of the distal surface of electrode 3. The end views of FIGS. 5a and 5c show the substantially semi-circular shape of the electrically exposed conductive portion 3a, and that electrically insulated portion 5a extends radially from aperture 7 to the periphery of the distal face 4. Electrically exposed conductive portion 3a does not fully or partially encircle aperture 7, but instead is lateral to aperture 7, and consequently does not form a ring-shaped electrode capable of coring tissue.

Figure 6:
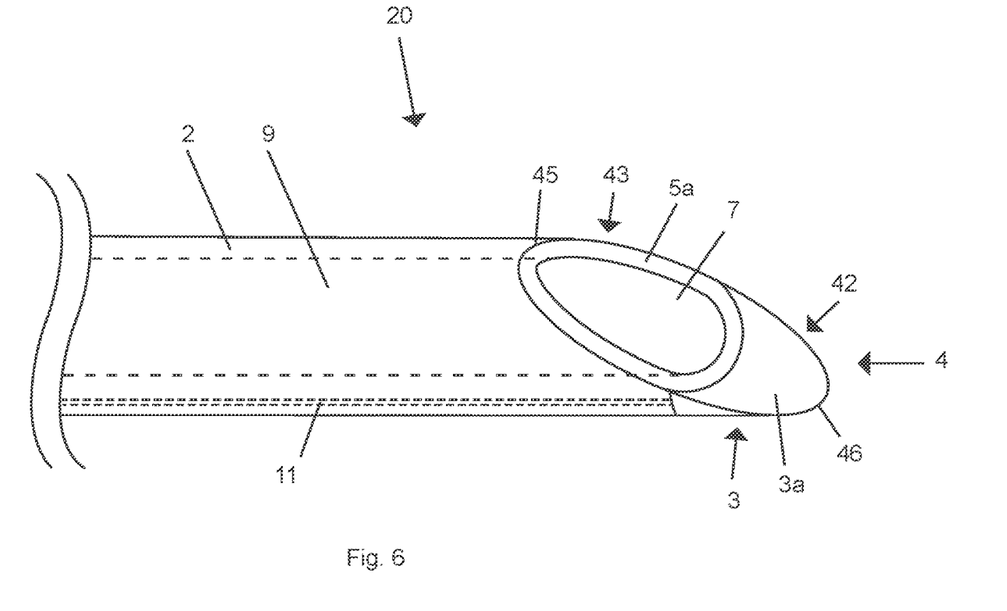
FIG. 6 is an illustration of an embodiment of a device with a non-conductive elongate member.

FIG. 6 illustrates an embodiment of energy delivery device 20 having a non-conductive elongate member 2, typically comprised of a polymer. Electrode 3 is attached to the end of the elongate member.

The embodiment of FIG. 6 has a beveled distal face 4. The electrically exposed conductive portion 3a of distal face 4 comprises a distal surface of electrode 3 and is generally crescent-shaped. Wire 11 is connected to electrode 3 for delivering energy thereto. In typical embodiments, wire 11 is contained in a lumen of appropriate size. Alternatively, wire 11 is embedded in a wall of the non-conductive elongate member 2.

In the illustrated embodiment, the electrically insulated portion 5a is located at a proximal portion of distal face 4 and is comprised of the distal surface of the non-conductive elongate member 2. When the embodiment of FIG. 6 is viewed from the end, electrically insulated portion 5a encircles aperture 7, and electrically exposed conductive portion 3a does not encircle the aperture, but instead is lateral to the aperture, and consequently does not form a ring-shaped electrode capable of coring tissue.

Figure 7A:
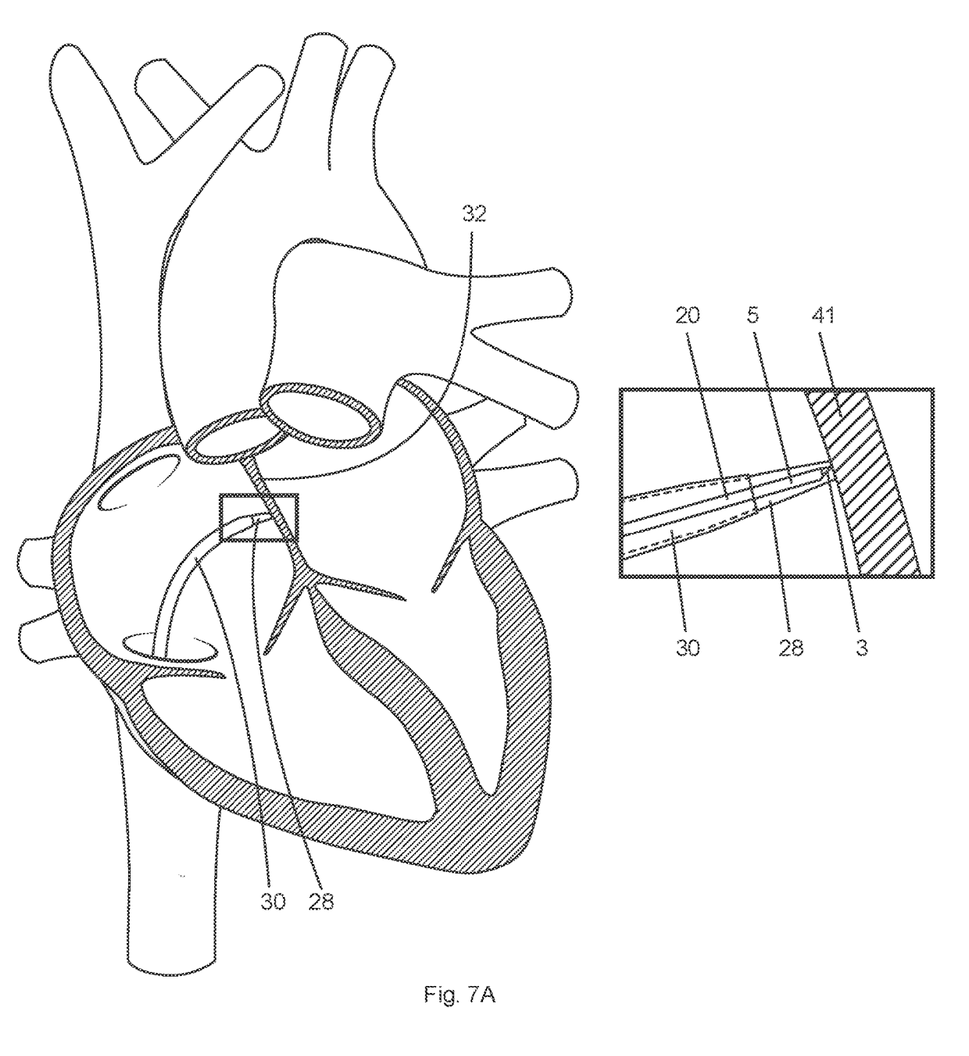
FIGS. 7a and 7b are illustrations of an embodiment of a method of puncturing tissue within a heart.
Figure 7B:
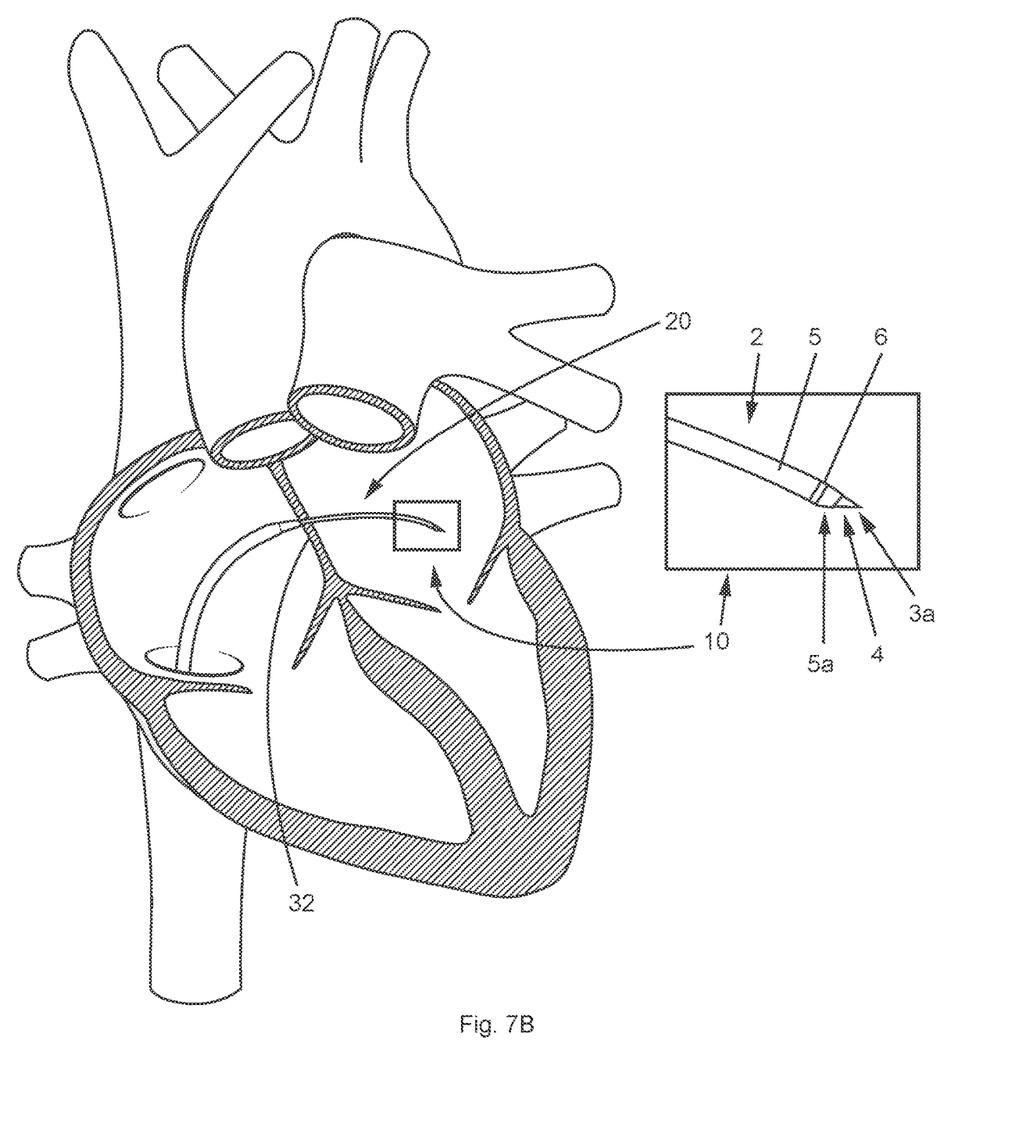

FIGS. 7a and 7b illustrate an embodiment of a method of puncturing tissue. The method comprises the steps of (a) delivering energy through electrically exposed conductive portion 3a of energy delivery device 20 to tissue 41 at a target site for creating a puncture substantially corresponding to a distal surface of the electrically exposed conductive portion; and (b) dilating the puncture primarily by advancing an angled distal surface of the energy delivery device, without coring the tissue. In some embodiments the step of delivering energy comprises creating a flap in the tissue and the step of dilating is completed without further delivery of energy. In some embodiments, the target site is a tissue within a heart, and in some particular embodiments the tissue is an atrial septum 32. Typically, the method requires the use of a sheath, such as sheath 30 of FIG. 7a.

An alternative embodiment of a method of puncturing tissue comprises the steps of (a) delivering energy through a first portion of a distal face of an energy delivery device to tissue at a target site to create a puncture through the tissue, while preventing delivery of energy from a second portion of the distal face; and (b) advancing the energy delivery device through the tissue by pushing aside a flap of tissue defined by the puncture. The step of delivering energy comprises creating a slit in the tissue.

Dilating the puncture typically includes displacing the tissue. In some embodiments, dilation includes wedging apart and thereby outwardly compressing surrounding portions of the tissue.

Some embodiments of the method include using a medical imaging modality to guide the energy delivery device 20 to the target site. Some embodiments comprise measuring pressure for positioning energy delivery device at the target site. In some embodiments, the method includes using a radiopaque marker 6 for positioning energy delivery device 20. Some embodiments include advancing the energy delivery device to the target site over a guide-wire.

In some embodiments, the method includes advancing energy delivery device 20 to the target site through a dilator 28; positioning energy delivery device 20 such that electrically exposed conductive portion 3a is aligned with or protruding slightly from a distal end of the dilator 28; and delivering fluid through an aperture at a distal end of energy delivery device 20 to stain the target tissue. The fluid is typically delivered longitudinally forward through the energy delivery device. Some embodiments further comprise a step of withdrawing a fluid via an open distal face of the energy delivery device.

In some embodiments, the distal surface of the electrically exposed conductive portion 3a is generally C-shaped and step (b) includes creating a generally C-shaped puncture. In some other embodiments, the distal surface of the electrically exposed conductive portion is generally crescent-shaped and step (b) includes creating a generally crescent-shaped puncture.

In some embodiments of the broad aspect, the aperture 7 and the lumen 9 together comprise a pressure transmitting lumen, and the method further comprises a step of measuring a fluid pressure within the pressure transmitting lumen using a pressure sensing mechanism.

In an RF perforation or puncturing procedure, energy is applied to rapidly increase tissue temperature to the extent that the intracellular fluid converts to steam, inducing cell lysis as a result of elevated pressure within the cell. Upon cell lysis and rupture, a void is created, allowing the tip of the energy delivery device to penetrate the tissue. In order to achieve this effect, RF perforation devices must apply a high voltage to the tissue region over a short period of time. Also, the tip of the device should be relatively small in order to increase the impedance of the device. This mechanism is in contrast to RF ablation, whereby a larger-tipped device is utilized to deliver a low impedance and high power signal to the region involved. Furthermore, the objective of RF ablation is to create a large, non-penetrating lesion in the tissue, in order to disrupt electrical conduction, as opposed to the objective of RF perforation, which is to create a void in the tissue. Thus, for the purposes of the present invention, perforation is defined as the creation of a void within a material.

Embodiments of the present invention are operable to create such punctures or voids without substantially removing a plug or core of material from the tissue at the target site, since the punctures are typically slit-like, C-shaped, or similar configurations corresponding to the shape(s) of the electrically exposed and conductive portion of the distal face.

Energy delivery device 20 may be used in conjunction with a source of radiofrequency energy suitable for perforating material within a patient's body. The source of energy may be a radiofrequency (RF) electrical generator, operable in the range of about 100 kHz to about 1000 kHz, and designed to generate a high voltage over a short period of time. More specifically, in some embodiments, the voltage generated by the generator increases from about 0 V (peak-to-peak) to greater than about 75 V (peak-to-peak) in less than about 0.6 seconds. The maximum voltage generated by generator may be between about 180V (peak-to-peak) and about 3000V (peak-to-peak). The waveform generated may vary, and may include a sine-wave, a rectangular-wave, or a pulsed rectangular wave, amongst others. During delivery of radiofrequency energy, the impedance load may increase due to occurrences such as tissue lesioning near the target-site, or the formation of a vapor layer following cell rupture. The generator may be operable to continue to increase the voltage, even as the impedance load increases. For example, energy may be delivered to a tissue within a body at a voltage that rapidly increases from about 0 V (RMS) to about 220 V (RMS) for a period of between about 0.5 seconds and about 5 seconds.

Without being limited to a particular theory of operation, it is believed that under particular circumstances, dielectric breakdown and arcing may occur upon the delivery of radiofrequency energy, whereby polar molecules may be pulled apart. The combination of these factors may result in the creation of an insulative vapor layer around the electrode, resulting in an increase in impedance, for example, impedance greater than 4000Ω In some embodiments, despite this high impedance, the voltage continues to increase. Further increasing the voltage increases the intensity of fulguration, which may be desirable as it allows for an increased perforation rate and puncture creation. An example of an appropriate generator for this application is the BMC RF Perforation Generator (model number RFP-100A, Baylis Medical Company, Montreal, Canada). This generator delivers continuous RF energy at about 460 kHz.

A grounding pad or dispersive electrode may be electrically coupled to the generator for contacting or attaching to the patient's body to provide a return path for the RF energy when the generator is operated in a monopolar mode.

Additional details regarding the device and method may be found in U.S. application Ser. No. 13/468,939, filed May 10, 2012, U.S. application Ser. No. 11/905,447, filed Oct. 1, 2007 (now issued as U.S. Pat. No. 8,192,425), U.S. application Ser. No. 13/113,326, filed May 23, 2007, U.S. application Ser. No. 11/265,304, filed Nov. 3, 2005 (now U.S. Pat. No. 7,947,040), U.S. application Ser. No. 10/666,301, filed Sep. 19, 2003 (now issued as U.S. Pat. No. 7,048,733), U.S. application Ser. No. 10/760,479, filed Jan. 21, 2004 (now issued as U.S. Pat. No. 7,270,662), U.S. application Ser. No. 10/666,288, filed Sep. 19, 2003, U.S. application Ser. No. 10/347,366, filed Jan. 21, 2003 (now issued as U.S. Pat. No. 7,112,197), U.S. provisional application Ser. No. 60/522,753, filed Nov. 3, 2004, and provisional application Ser. No. 60/884,285, filed Jan. 10, 2007, 60/827,452, filed Sep. 29, 2006, Ser. No. 61/653,967, filed May 31, 2012, and Ser. No. 61/681,512, filed Aug. 9, 2012. The contents of all above-named applications and patents are incorporated herein by reference in their entirety.

Thus, the problem of puncturing tissue without coring, while providing forward fluid delivery, is solved by an energy delivery device having a distal face defining an opening, with the distal face including at least one electrically exposed portion and at least one electrically insulated portion.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. An energy delivery device comprising:
   an elongate member which substantially comprises a non-conductive material and defines a lumen for receiving a fluid;
   a distal face of the elongate member defining an aperture in communication with the lumen wherein all of the distal face defines a beveled surface; and
   the beveled surface of the distal face consisting of a single electrically exposed conductive portion and a single electrically insulated portion wherein the single electrically insulated portion completely surrounds and defines the aperture and the single electrically exposed conductive portion is lateral to and spaced apart from the aperture, the single electrically insulated portion extends radially from a wall of the aperture to a periphery of the distal face, and all of the single electrically insulated portion is proximal of at least some of the single electrically exposed conductive portion,
   the distal face being thereby configured to avoid creation of emboli upon delivery of energy via the single electrically exposed conductive portion.

2. The energy delivery device of claim 1, wherein the single electrically exposed conductive portion comprises a distal surface of a single electrode located at a furthest distal portion of the beveled surface.

3. The energy delivery device of claim 2, wherein the distal surface of the single electrode is generally crescent-shaped.

4. The energy delivery device of claim 2, wherein the single electrode defines a distal portion of an outside of a sidewall of the elongated member.

5. The energy delivery device of claim 2, wherein the single electrically insulated portion comprises a polymer located at a proximal portion of the distal face.

6. The energy delivery device of claim 5, wherein the single electrically insulated portion of the beveled surface encircles the aperture and only the single electrically insulated portion defines the aperture.

7. The energy delivery device of claim 2, further comprising a radiopaque marker for marking a location of the single electrode.

8. The energy delivery device of claim 7, wherein the radiopaque marker is embedded in a sidewall of the elongate member.

9. The energy delivery device of claim 1, wherein the elongate member has a sidewall which comprises a single layer of the non-conductive material and the sidewall does not comprise a layer of an electrically conductive material.

10. The energy delivery device of claim 1, wherein the elongate member has an outer diameter of about 0.40 mm to about 1.5 mm to minimize hemodynamic instability upon puncturing tissue.

11. The energy delivery device of claim 1, wherein the elongate member has a flexural rigidity of at least about 0.016 $Nm^2$.

12. The energy delivery device of claim 11, wherein the flexural rigidity is about 0.017 $Nm^2$.

13. The energy delivery device of claim 11, wherein the elongate member comprises a normally curved section wherein a distal section of the elongate member which is distal to the normally curved section is orientated in a different direction than a proximal section of the elongate member which is proximal to the normally curved section.

14. The energy delivery device of claim 13, wherein the normally curved section has a curve length from about 10 cm to about 25 cm and traverses from about 20° to about 40° of a circle.

15. The energy delivery device of claim 13, wherein the normally curved section has a curve length from about 4 cm to about 7 cm and traverses from about 70 degrees to about 110 degrees of a circle.

16. The energy delivery device of claim 1, further comprising a handle coupled to a proximal end of the elongate member.

17. The energy delivery device of claim 16, wherein the handle comprises an electrical connector operable to be coupled to an electrosurgical generator.

18. The energy delivery device of claim 16, wherein the handle comprises a fluid port for allowing for fluid communication between the lumen and a source of fluid.

19. The energy delivery device of claim 16, wherein the handle comprises a plurality of ridges for transmitting tactile feedback.

20. The energy delivery device of claim 1, wherein the elongate member has a length of about 30 cm to about 100 cm to facilitate a puncture of a septum of a heart.

* * * * *